(12) United States Patent
Bernard et al.

(10) Patent No.: US 6,495,689 B2
(45) Date of Patent: Dec. 17, 2002

(54) SYNTHESIS OF INTERMEDIATES USEFUL IN PREPARING TRICYCLIC COMPOUNDS

(75) Inventors: Charles F. Bernard, Agoura Hills, CA (US); Michael Casey, Dublin (IE); Frank Xing Chen, Plainsboro, NJ (US); Denise C. Grogan, Cork (IE); Marc Poirier, Edison, NJ (US); Robert P. Williams, Enniskerry (IE); Yee-Shing Wong, Florham Park, NJ (US); George G. Wu, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/886,845

(22) Filed: Jun. 21, 2001

(65) Prior Publication Data

US 2002/0077331 A1 Jun. 20, 2002

Related U.S. Application Data

(62) Division of application No. 09/442,512, filed on Nov. 18, 1999, now Pat. No. 6,372,909.
(60) Provisional application No. 60/109,211, filed on Nov. 20, 1998.

(51) Int. Cl.[7] ............................................. C07D 221/16
(52) U.S. Cl. ........................................................ 546/93
(58) Field of Search ................................................ 546/93

(56) References Cited

U.S. PATENT DOCUMENTS

| | | | | |
|---|---|---|---|---|
| 4,282,233 A | | 8/1981 | Vilani | ........................ 424/267 |
| 5,151,423 A | | 9/1992 | Piwinski et al. | ............ 514/254 |

FOREIGN PATENT DOCUMENTS

| | | |
|---|---|---|
| EP | 0 208 855 | 5/1986 |
| EP | 0 582 825 | 2/1990 |
| EP | 0 806 415 | 4/1997 |
| WO | WO 96/31478 | 10/1996 |
| WO | WO 97/23478 | 7/1997 |
| WO | WO 9/42676 | 10/1998 |

*Primary Examiner*—Patricia L. Morris
(74) *Attorney, Agent, or Firm*—William Y. Lee; Arthur Mann

(57) ABSTRACT

Disclosed is a process for preparing a compound having the formula:

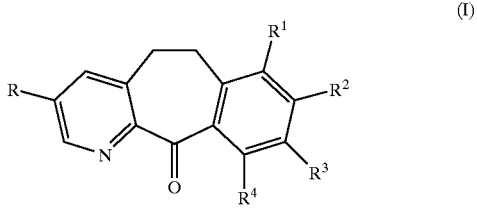

wherein R, $R^1$, $R^2$, $R^3$, and $R^4$ are independently selected from the group consisting of H, Br, Cl, F, alkyl, or alkoxy.

5 Claims, No Drawings

SYNTHESIS OF INTERMEDIATES USEFUL IN PREPARING TRICYCLIC COMPOUNDS

This application is a divisional of U.S. Ser. No. 09/442,512, filed on Nov. 18, 1999, now U.S. Pat. No. 6,372,909, which claims the benefit of U.S. Provisional Application No. 60/109,211, filed Nov. 20, 1998.

BACKGROUND OF THE INVENTION

This invention provides an improved process for preparing intermediates useful in the preparation of tricyclic compounds known as antihistamines and as inhibitors of farnesyl protein transferase (FPT). In particular, the compounds of this invention are useful in the preparation of antihistamines such as those disclosed in U.S. Pat. Nos. 4,282,233 and 5,151,423, and of FPT inhibitors disclosed in PCT Publication No. WO97/23478, published Jul. 3, 1997.

SUMMARY OF THE INVENTION

This invention provides a process for preparing a compound having the formula:

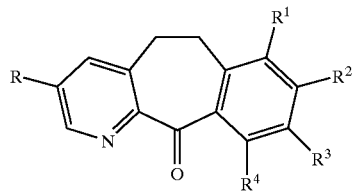

(I)

wherein R, $R^1$, $R^2$, $R^3$, and $R^4$ are independently selected from the group consisting of H, Br, Cl, F, alkyl, or alkoxy, said process comprising:

(A) reacting a compound having the formula

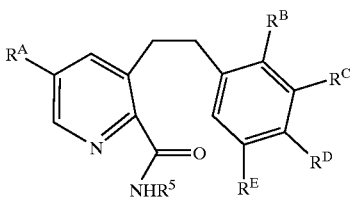

(II)

wherein $R^A$, $R^B$, $R^C$, $R^D$, and $R^E$ are independently selected from the group consisting of H, halo, alkyl, or alkoxy, and $R^5$ is aryl or heteroaryl, with a dehydrating agent to produce an imine having the formula:

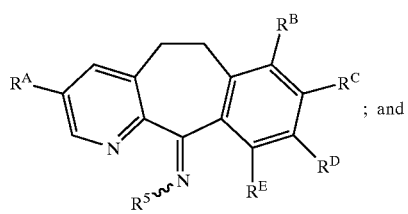

; and (B) hydrolyzing the imine produced in step (A) to produce the compound having formula (I).

This invention also provides novel intermediates having the formula

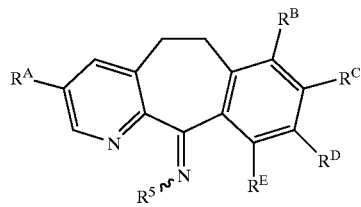

wherein $R^A$, $R^B$, $R^C$, $R^D$, and $R^E$ are independently selected from the group consisting of H, halo, alkyl, or alkoxy, and $R^5$ is aryl or heteroaryl.

This invention further provides a process for preparing a compound having the formula:

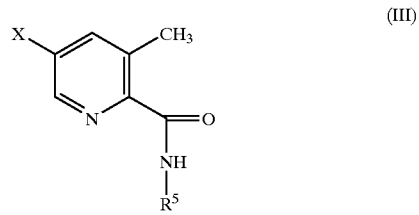

(III)

comprising:
reacting a compound having the formula:

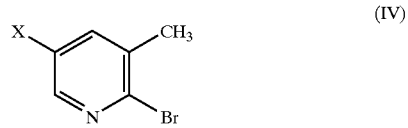

(IV)

with $NH_2R^5$ in the presence of a palladium catalyst, carbon monoxide, a base, and an ether selected from the group consisting of: ethylene glycol dimethyl ether (i.e., $CH_3OCH_2CH_2OCH_3$); 2-methoxyethyl ether (i.e, $CH_3OCH_2CH_2OCH_2CH_2OCH_3$); and triethylene glycol dimethyl ether (i.e, $CH_3OCH_2CH_2OCH_2CH_2OCH_2CH_2OCH_3$), wherein X is H, Br, Cl, or F, and $R^5$ is aryl or heteroaryl. The compounds of formula III can be reacted with compounds having the formula

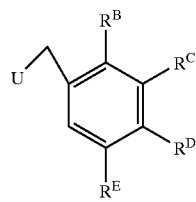

wherein U is Br or Cl and $R^B$, $R^C$, $R^D$, and $R^E$ are as defined above, in the presence of a strong base to provide compounds having the formula II, wherein $R^A$ is Br, Cl or F.

DETAILED DESCRIPTION

As used herein, the term "alkyl" means straight or branched hydrocarbon chains of 1 to 6 carbon atoms.

"Halo" refers to fluorine, chlorine, bromine or iodine radicals.

"Aryl" means phenyl; benzyl; or a polyaromatic ring (e.g., napthyl), each of the foregoing being optionally substituted by 1 to 3 substituents independently selected from the group consisting of $C_1$ to $C_6$ alkyl, $C_1$ to $C_6$ alkoxy, and halo.

"Heteroaryl" means a 5- or 6-membered aromatic ring having one or two nitrogen atoms, e.g., pyridyl, pyrimidyl, imidazolyl or pyrrolyl.

"Ac" refers to acetyl.

"Et" refers to —$C_2H_5$.

"Ph" refers to phenyl.

The present process is a significant improvement over prior art processes for preparing the tricyclic ketone of formula (I). For example, U.S. Pat. No. 4,731,447 discloses the following process:

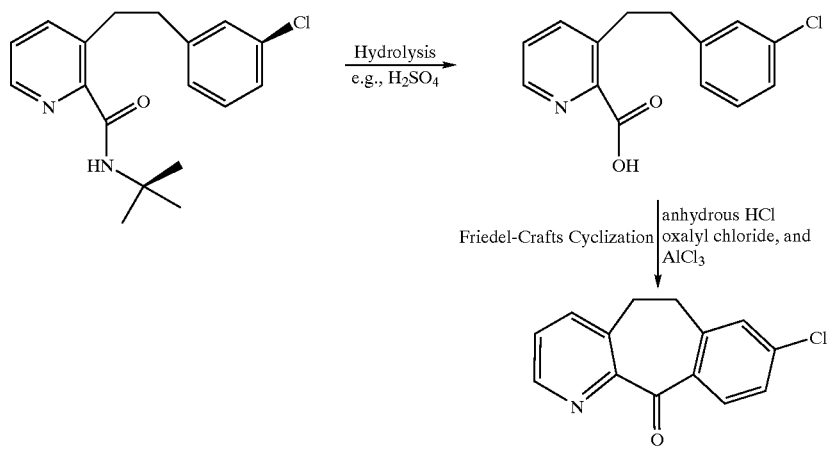

In contrast to this process, in which the product from the hydrolysis step must be isolated and purified prior to the next step (the Friedel-Crafts cyclization), the present process for preparing compounds of formula (I) offers a more simplified synthesis that can be carried out in one pot.

PCT Publication WO96/31478, published Oct. 10, 1996, discloses the following process:

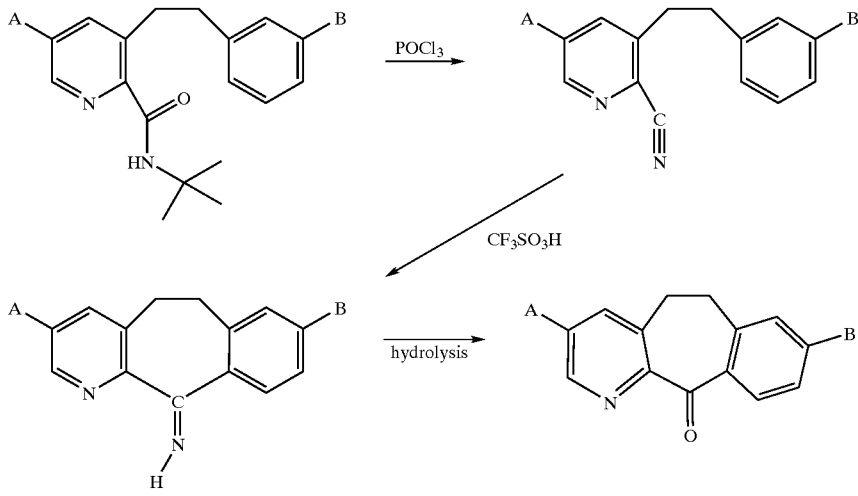

In this process, a tert-butyl substituted compound is reacted with $POCl_3$ in toluene at reflux to form the nitrile, the nitrile is reacted with $CF_3SO_3H$ to form an imine, and the imine is hydrolyzed to form the ketone. Again, in contrast to this process, which is a two-pot process, because the nitrile must be isolated and purified prior to reaction with $CF_3SO_3H$, the present process can be carried out in one pot.

The compounds prepared by the present process are useful as intermediates in the procedures described in PCT Publication No. WO97/23478 and U.S. Pat. No. 5,151,423 to obtain the desired compounds wherein the piperidinyl ring is N-substituted. Using those procedures, the compounds of the present invention are reacted with a substituted piperidine of the formula wherein $L^1$ is a leaving group selected from the group consisting of Cl and Br, to obtain a compound of the formula

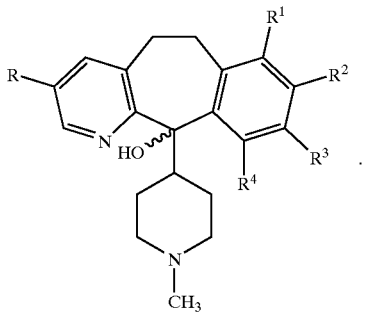

This compound is converted to the corresponding piperidylidene, the nitrogen is deprotected, and the compound is reduced to the piperidyl form. The piperidinyl nitrogen can then be reacted with a variety of compounds, e.g., an acyl compound such as an ester or acyl chloride to form the desired amide.

Alternatively, when chiral FPT inhibitors, such as those described in PCT Publication No. WO97/23478 are desired, the compounds made by the present process may be reduced by treating with Zn and 2 equivalents of trifluoroacetic acid in acetic anhydride to remove the carbonyl oxygen. The reduced compound can then be reacted with about 3.5 equivalents of lithium diisopropylamide, about 1.3 equivalents of quinine or a compound of the formula

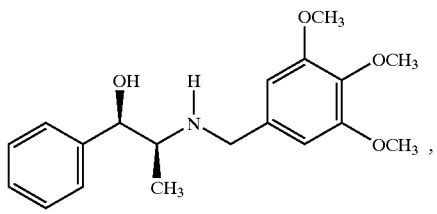

about 1.2 equivalents of 4-mesyl-N-Boc-piperidine, and about 1.1 equivalents of water in toluene to form the following chiral compound:

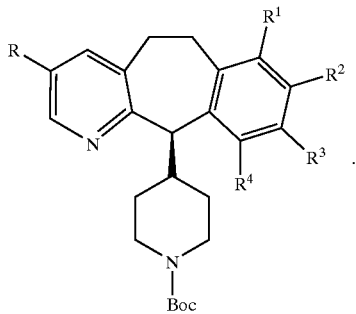

This chiral compound can then be deprotected by treatment with acid (e.g., $H_2SO_4$), reacted with a suitable acid (e.g., N-acetyl-L-phenylalanine) to form a stable salt, and the stable salt can then be acylated with the desired acyl group.

Compounds of formula (I) can be converted to other compounds of formula (I) by methods known in the art, i.e., compounds wherein R, $R^1$, $R^2$, $R^3$ or $R^4$ is hydrogen can be converted to the corresponding compounds wherein R, $R^1$, $R^2$, $R^3$ or $R^4$ is halogen. Such procedures are shown in WO97/23478, wherein, for example, a compound wherein $R^2$ is Cl, $R^1$, $R^3$ and $R^4$ are hydrogen and the piperidinyl nitrogen is protected by a —$COOCH_2CH_3$ group is reacted with $KNO_3$, the resulting nitro-substituted compound is reduced to the amine, the resulting compound is reacted with $Br_2$ and the amino group is removed to obtain a compound wherein $R^2$ is Cl, $R^4$ is Br and $R^1$ and $R^3$ are hydrogen.

Preferred compounds of formula (I) are those in which $R^2$ is Cl, Br or F, more preferably Cl or Br, most preferably, Cl. Another group of preferred compounds are those in which R, $R^1$, $R^3$ and $R^4$ are each hydrogen, and $R^2$ is Cl, Br or F, more preferably Cl or Br, most preferably, Cl. Still another group of preferred compounds are those in which $R^1$, $R^3$, and $R^4$ are each hydrogen and R and $R^2$ are independently selected from Cl, Br and F, more preferably from Cl and Br, and most preferably, in which R is Br and $R^2$ is Cl. Yet another group of preferred compounds are those in which $R^1$ and $R^3$ are each hydrogen, and R, $R^2$ and $R^4$ are independently selected from Cl, Br and F, more preferably from Cl and Br, and most preferably, in which R is Br, $R^2$ is Cl and $R^4$ is Br. These preferred compounds may be made from compounds of formula (II) having correspondingly positioned halo substituents. It will be appreciated by those skilled in the art that when the compounds of formula (II) have iodo substituents, those iodo substituents are displaced by H when the present process is carried out.

$R^5$ is preferably aryl, most preferably, phenyl, 4-methoxyphenyl, 4-chlorophenyl, or 3-chlorophenyl.

The dehydrating agent is preferably selected from the group consisting of $P_2O_5$, $P_2O_3$, $P_2O_3Cl_4$, $POCl_3$, $PCl_3$, $PCl_5$, $C_6H_5P(O)Cl_2$ (phenyl phosphonic dichloride), $PBr_3$, $PBr_5$, $SOCl_2$, $SOBr_2$, $COCl_2$, $H_2SO_4$, super acids, and anhydrides of super acids. More preferably, the dehydrating agent is selected from $P_2O_5$, $P_2O_3Cl_4$, $PBr_3$, $PCl_5$, $POCl_3$, $C_6H_5P(O)Cl_2$, $(CF_3SO_2)_2O$, and $(CF_3CF_3SO_2)_2O$.

Preferably, step (A) of our process is carried out by contacting the reaction mixture of the compound of formula (II) and the dehydrating agent with an additional agent selected from the group consisting of a Lewis acid or a super acid. Non-limitative examples of Lewis acids include $AlCl_3$, $FeCl_3$, $ZnCl_2$, $AlBr_3$, $ZnBr_2$, $TiCl_4$, and $SnCl_4$. Of the foregoing, $AlCl_3$, $ZnCl_2$, $FeCl_3$, $SnCl_4$, and $ZrBr_2$ are particularly preferred. Non-limitative examples of super acids include $CF_3SO_3H$,

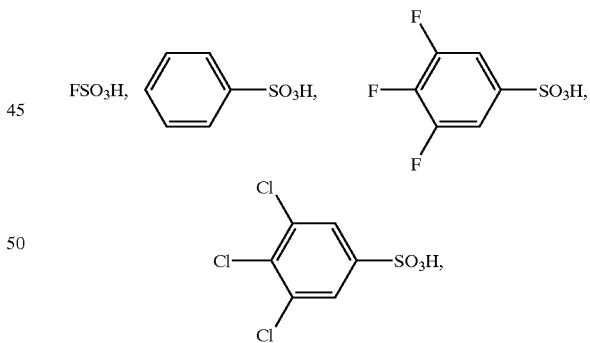

and $HF/BF_3$. Of the foregoing super acids, $CF_3SO_3H$ is particularly preferred. The contacting by the Lewis acid or the super acid may be accomplished by adding it prior to, contemporaneously with, or after the time at which the dehydrating agent is brought into contact with the compound of formula (II). Particularly preferred combinations of dehydrating agents and Lewis acids or super acids include $P_2O_5/CF_3SO_3H$, $PCl_5/AlCl_3$, $POCl_3/ZnCl_2$, $PCl_5/FeCl_3$, $PCl_5/SnCl_4$, and $POCl_3/ZnBr_2$.

When a dehydrating agent other than an anhydride is used in step (A), preferably the dehydrating agent is used in amounts ranging from 1 to 20 equivalents, more preferably, 1 to 10 equivalents, most preferably, 1.0 to 8.0 equivalents. When the dehydrating agent is an anhydride of a super acid, it is preferably used in amounts ranging from 0.5 to 10 equivalents, more preferably 1.0 to 5.0 equivalents, most preferably, 1.2 to 2.0 equivalents. When a Lewis acid is used in addition to the dehydrating agent, the Lewis acid is preferably used in amounts ranging from 1 to 20 equivalents, more preferably 1.5 to 10 equivalents, most preferably 2 to 5 equivalents. When a super acid is used in addition to the dehydrating agent, the super acid is preferably used in amounts ranging from 0.5 to 10 equivalents, more preferably, 1 to 5 equivalents, most preferably, 2 to 4 equivalents.

Step (A) is preferably carried out at a temperature of 10 to 120° C., more preferably, 15 to 90° C., most preferably 20 to 90° C. The time for reaction ranges from 1 to 60 hours, preferably 2 to 40 hours, most preferably 5 to 35 hours.

The imine formed in step (A) is preferably hydrolyzed by adding water, preferably in an amount ranging from 1 to 10 volumes of the amide of formula (II), more preferably 1.5 to 7 volumes, most preferably 2 to 5 volumes. The hydrolysis is preferably carried out at a temperature of from 20 to 120° C., more preferably from 30 to 100° C., most preferably from 40 to 80° C.

Preferably, steps (A) and (B) are carried out in an aprotic organic solvent. The aprotic organic solvent is preferably selected from dichloroethane, methylene chloride, benzene, and halogenated aromatic solvents, e.g., chlorobenzene, dichlorobenzene trichlorobenzene, and trifluoromethylbenzene.

The starting compounds of formula (II) may be prepared as shown in the following scheme:

As shown in the scheme above (wherein $R^A$, $R^B$, $R^C$, $R^D$, $R^E$, and $R^5$ are as defined previously), the pyridine compound 1 is reacted with $NH_2R^5$ in the presence of a palladium catalyst, (e.g., $Pd(OAc)_2$/dipyridyl or $(Ph_3P)_2\ PdCl_2$), carbon monoxide, and a base, in a suitable solvent (e.g., tetrahydrofuran ("THF"), dimethylformamide ("DMF"), acetonitrile ($CH_3CN$) and toluene, or combinations thereof, most preferably, $CH_3CN$) at a temperature of about 35° to 100° C., preferably about 55° C., and a pressure of about 5 psi to 500 psi, preferably about 50 to 150 psi, to form amide compound 2. Non-limitative examples of suitable bases for the foregoing reaction include $C_1$ to $C_{10}$ alkyl amines, such as triethylamine, tri-n-butylamine and 1,8-diazabicyclo-[5.4.0]undec-7-ene ("DBU"), and inorganic bases such as $K_2CO_3$, $Na2CO_3$, $Na2HPO_4$ and NaOH. Preferably, the base is selected from $K_2CO_3$, DBU, and triethylamine, with DBU being preferred for use with $Pd(OAc)_2$/dipyridyl, and triethylamine being preferred for use with $(Ph_3P)_2\ PdCl_2$. Amide compound 2 is reacted with compound 3 in the presence of a strong base (e.g., lithium diisopropylamide ("LDA"), n-butyl lithium, lithium hexamethyldisilylamide, or sodium amide, preferably LDA or n-butyl lithium) in a suitable solvent, e.g., THF, at a temperature of about 50° C. to 20° C., preferably about −30° C. to −20° C. to form the compound of formula (II).

Alternatively, the amide compound 2 may be prepared as shown in the scheme below:

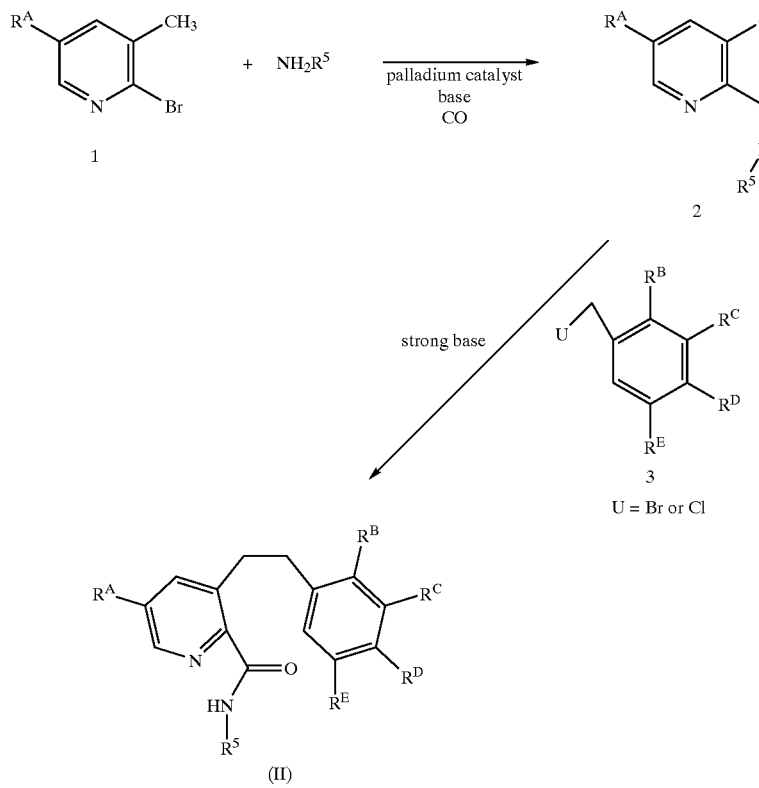

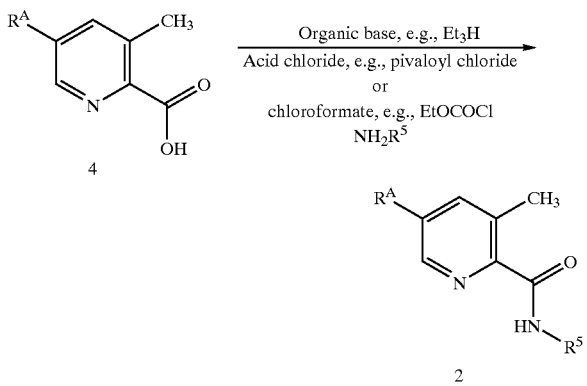

Picolinic acid compound 4 is reacted with an organic base, e.g., triethylamine, followed by an acid chloride, e.g., pivaloyl chloride or a chloroformate, e.g., $C_2H_5OCOCl$ in a suitable solvent such as dichloromethane at a temperature of about −30° C. to 0° C. to give a mixed anhydride. To the mixture is added $NH_2R^5$ at a temperature of −30° C. to 0° C. either neat or as a solution in a suitable solvent to form amide compound 2.

The process for preparing compounds of formula (111) from compounds of formula (IV) is carried out by reacting the compound of formula (IV) with $NH_5R^5$ in the presence of a palladium catalyst, carbon monoxide, a base, and an ether selected from the group consisting of: ethylene glycol dimethyl ether (i.e., $CH_3OCH_2CH_2OCH_3$); 2-methoxyethyl ether (i.e, $CH_3OCH_2CH_2OCH_2CH_2OCH_3$); and triethylene glycol dimethyl ether (i.e, $CH_3OCH_2CH_2OCH_2CH_2OCH_2CH_2OCH_3$). X is preferably Br, Cl or F, most preferably, Br, and $R^5$ is preferably phenyl, 4-methoxyphenyl, 4-chlorophenyl, or 3-chlorophenyl. Non-limitative examples of palladium catalysts that may be used in this process, include $Pd(OAc)_2$, $PdCl_2$, $(PPh_3)_2PdCl_2$, $PdBr_2$, and $(PPh_3)_4Pd$. $Pd(OAc)_2$ and $PdCl_2$ are particularly preferred. This process is preferably carried out at at a temperature of about 35° to 120° C., preferably about 40 to 100° C., most preferably about 45 to 90° C., and a pressure of about 5 psi to 500 psi, preferably about 30 to 150 psi, most preferably about 40 to 100 psi. Non-limitative examples of suitable bases for this process include $C_1$ to $C_{10}$ alkyl amines, such as diisopropylethylamine, diisopropylbenzylamine, tri-n-butylamine, triisopropylamine, triethylamine, t-butylamine and 1,8-diazabicyclo-[5.4.0]undec-7-ene ("DBU"), and inorganic bases such as $K_2CO_3$, $KHCO_3$, $Na_2CO_3$, $NaHCO_3$, $Na_3PO_3$, $Na2HPO_4$, and $NaOH$. Preferably, the base is selected from $K_2CO_3$, DBU, triethylamine, and diisopropylethylamine, and most preferably, is selected from DBU and diisopropylethylamine. Preferably, this process is carried out in a solvent in addition to the ethylene glycol dimethyl ether, or 2-methoxyethyl ether, or triethylene glycol dimethyl ether. Non-limitative examples of suitable solvents include toluene, chlorobenzene, dichlorobenzene, acetonitrile, trifluoromethylbenzene, N,N-dimethylformamide, N,N-dimethylacetamide, tetrahydrofuran, and xylene, with toluene, and chlorobenzene being particularly preferred. Because the ethylene glycol dimethyl ether, or 2-methoxyethyl ether, or triethylene glycol dimethyl ether functions as a ligand for the palladium catalyst, this process can be carried out without having to use dipyridyl as a ligand. The amount of $NH_2R^5$ used preferably ranges from 0.9 to 5 equivalents, more preferably from 1.0 to 3 equivalents, most preferably from 1.1 to 1.5 equivalents.

The amount of base preferably ranges from 0.8 to 10 equivalents, more preferably from 1.0 to 5 equivalents, most preferably from 1.2 to 2.0 equivalents. The amount of ethylene glycol dimethyl ether, or 2-methoxyethyl ether, or triethylene glycol dimethyl ether is preferably from 0.2 to 5.0 volumes of 2,5-dibromo-3-methylpyridne used, more preferably from 0.4 to 2.0 volumes, most preferably from 0.5 to 1.5 volumes. The amount of additional solvent (e.g., toluene or chlorobenzene) preferably ranges from 1.0 to 20 volumes of the 2,5-dibromo-3-methylpyridine used, more preferably from 1.5 to 10 volumes, most preferably from 2 to 5 volumes.

The starting materials used in the foregoing processes, i.e., compound 1, $NHR^2R^5$, compound 3, and compound 4, are known in the art or can readily be prepared by one skilled in the art.

The following examples illustrate the foregoing invention, although such examples should not be construed as limiting the scope of the invention. Alternative reagents and analagous processes within the scope of the invention will be apparent to those skilled in the art.

EXAMPLE A

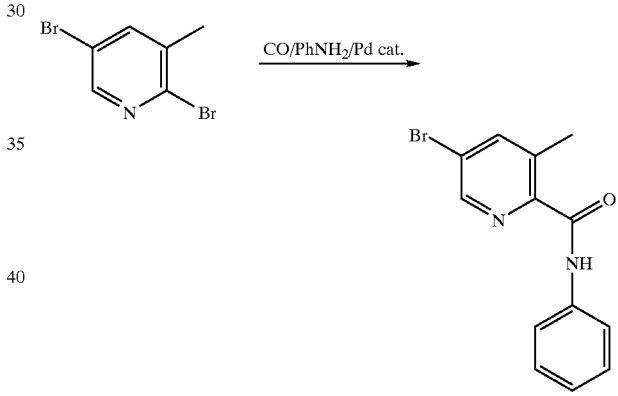

To a 4 L autoclave were added sequentially 250 g (949 mmol) of 2,5-dibromo-3-methylpyridine, 4.5 g (20 mmol) of $Pd(OAc)_2$, 127 mL (1.1 mol) of aniline, 210 mL (1.4 mol) of 1,8-diazabicyclo[5,4,0]undec-7-ene, 500 mL of toluene, and 250 mL of ethylene glycol dimethyl ether. The autoclave was sealed, evacuated, purged with nitrogen, and charged with carbon monoxide to 80 psi. The reaction mixture was heated to 65° C. for about 2 days with periodical refilling if necessary, and then cooled to room temperature. The content in the autoclave was vented under vacuum, flushed with nitrogen, and transferred to a 10 L flask with the aid of water and toluene. To the mixture were added 25 g of Darco and 25 g of Supercel. The contents were filtered through a pad of celite and washed with toluene. The filtrate was extracted with 2×1 L of toluene. The combined extract was washed with brine, and concentrated to 750 mL. The residual toluene was chased with isopropanol (i-PrOH). The residue was recrystallized from hot i-PrOH and the precipitated was filtered, washed with i-PrOH, and dried at 50° C. to give 220 g (76%) of the amide as a white solid.

PREPARATION 1

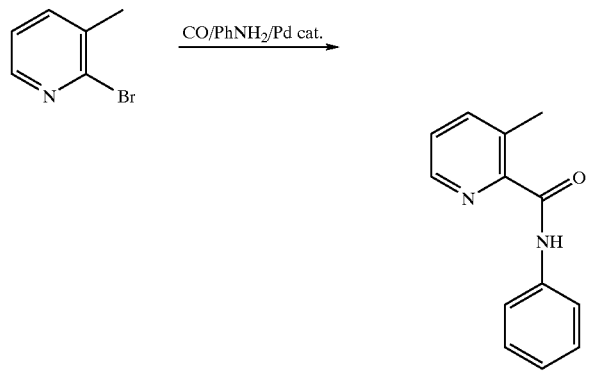

To a 4 L autoclave were added sequentially 400 g (2.21 mol) of 2-bromo-3-methylpyridine, 8.2 g (12 mmol) of $(Ph_3P)_2PdCl_2$, 1.0 L of acetonitrile, 295 g (3.16 mol) of aniline, and 515 g (3.38 mmol) of DBU. The autoclave was sealed, evacuated, purged with nitrogen, and charged with carbon monoxide to 80 psi. The reaction mixture was heated to 65° C. for 9 hours with periodical refilling of carbon monoxide if necessary, and then cooled to room temperature. The content of the autoclave was vented under vacuum, flushed with nitrogen and transferred into a separatory funnel with the aid of water and acetonitrile. To the mixture were added 40 g of Darco and 40 g of Supercel. The contents were stirred for 30 min, filtered and washed with acetonitrile. The filtrate was concentrated to a final volume of 1.6 L. Addition of 3.0 L of water precipitates the product as a yellow solid. The solid was filtered and dried to give 427 g amide (90%). Mp. 66–67° C. $^1$H NMR (CDCl$_3$): δ 10.23 (bs, 1H), 8.37 (dd, J=4.6 Hz, 0.8 Hz, 1H), 7.71 (m, 2H), 7.62 (dd, J=6.95 Hz, 1H), 7.31–7.36 (m, 3H), 7.10 (t, J=7.42 Hz, 1H), 2.79 (s, 3H). $^{13}$C NMR (CDCl$^3$): δ 163.52, 146.70, 145.21, 141.28, 138.02, 136.13, 128.94, 125.95, 123.97, 119.62, 20.80. IR: 3330 (w), 2920 (s), 1680 (m) cm$^{-1}$. Analysis. Calcd for $C_{13}H_{12}N_2O$: C, 73.58, H, 5.66, N, 13.21; found: C, 73.29, H, 5.76, N, 12.81.

PREPARATION 2

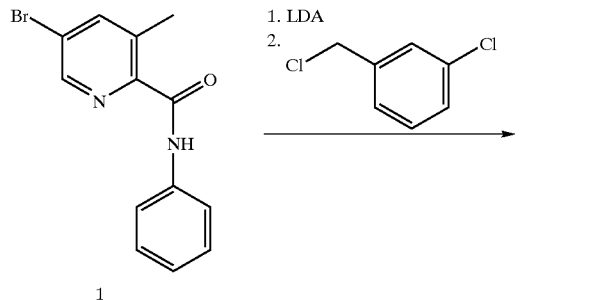

To a –25° C. solution of amide 1 (50 g, 0.168 mol) in THF (400 mL) and diisopropylamine (7.05 mL, 0.050 mol) was added a 1.5 M solution of lithium diisopropylamine mono (tetrahydrofuran) (225 mL, 0.336 mol) dropwise. The resulting dianion solution was aged for 1 hour at a temperature between –20° C. and –25° C. and was quenched with 3-chlorobenzylchloride (22.0 mL, 0.176 mol). The mixture was allowed to warm to 0° C. and, after 1 hour, was quenched into a saturated aqueous solution of NH$_4$Cl. The phases were separated and the aqueous layer was extracted with t-Butyl methyl ether (350 mL). The combined organic solution was washed with a brine solution and concentrated to an oil. The product was then crystallized in isopropyl alcohol (200 mL) to give 62.7 g (89.8%) of the coupled product. Mp 102–103° C. $^1$H NMR (CDCl$_3$): δ 10.07 (s, 1H), 8.56 (d, J=2.1 Hz, 1H), 7.77 (dd, J=8.7 Hz, 1.1 Hz, 2H), 7.70 (d, J=2.1 Hz, 1H), 7.42 (t, J=8.4 Hz, 2H), 7.28 (d, J=2.4 Hz, 1H), 7.16–7.25 (m, 4H), 3.49–3.53 (m, 2H), 2.99–3.03 (m, 2H). $^{13}$C NMR (CDCl$_3$): δ 162.45, 146.85, 145.17, 143.16, 142.95, 140.95, 137.70, 134.10, 129.63, 129.06, 128.74, 126.90, 126.33, 124.36, 123.24, 119.84, 36.91, 35.35. IR: 2930 (s), 1690 (m) cm$^{-1}$. Anal. Calcd. for $C_{20}H_{16}BrClN_2O$: C, 57.83, H, 3.85, N, 6.75; Found: C, 58.05, H, 4.06, N, 6.80.

PREPARATION 3

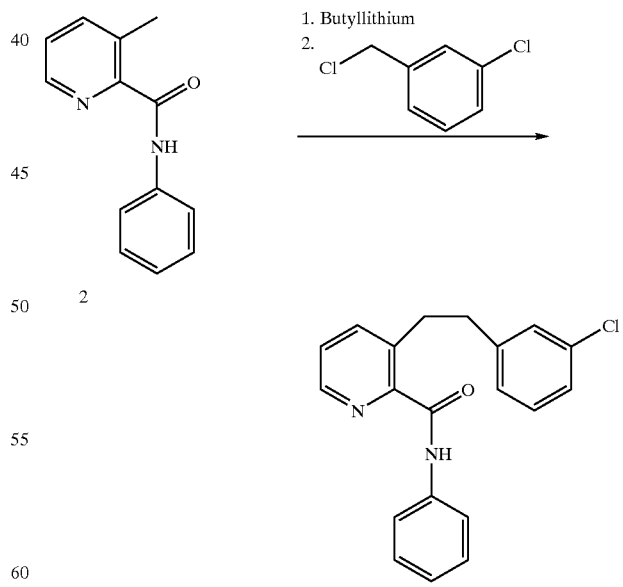

To a –25° C. solution of amide 2 (50 g, 0.231 mol) in THF (500 mL) was added a 2.5M solution of Butyllithium in Hexanes (185 mL, 0.462 mol) dropwise. The resulting dianion solution was aged for 1 hour at a temperature between –20° C. and –25° C. and was quenched with 3-chlorobenzylchloride (31.0 mL, 0.248 mol). The mixture was allowed to warm to 0° C. and, after 1 hour, was quenched into a saturated aqueous solution of NH$_4$Cl. The phases were separated and the aqueous layer was extracted with t-Butyl methyl ether (350 mL). The combined organic solution was washed with a brine solution and was concentrated to an oil. The product was then crystallized in isopropyl alcohol (200 mL) to give 71.6 g (91.5%) of the coupled product. Mp 80–81° C. $^1$H NMR (CDCl$_3$) δ 10.23 (s, 1H), 8.48 (dd, J=4.6 Hz, 1.6 Hz, 1H), 7.78 (dd, J=0.8 Hz, 8.4 Hz, 2H), 7.48 (dd, J=7.9 Hz, 1.5 Hz, 1H), 7.39–7.12 (m, 8H), 3.45–3.50 (m, 2H), 3.02–2.98 (m, 2H). $^{13}$C NMR (CDCl$_3$) δ 164.09, 147.63, 146.72, 144.63, 141.91, 140.16, 138.97, 134.98, 130.55, 130.05, 129.82, 128.03, 127.16, 127.03, 125.17, 120.84, 38.30, 36.77. IR: 2930 (s), 1690 (m) cm$^{-1}$. Anal: Calcd for C$_{20}$H$_{17}$ClN$_2$O: C, 71.43, H, 5.06, N, 8.33; Found: C, 71.37, H, 5.12, N, 8.35.

EXAMPLE 1

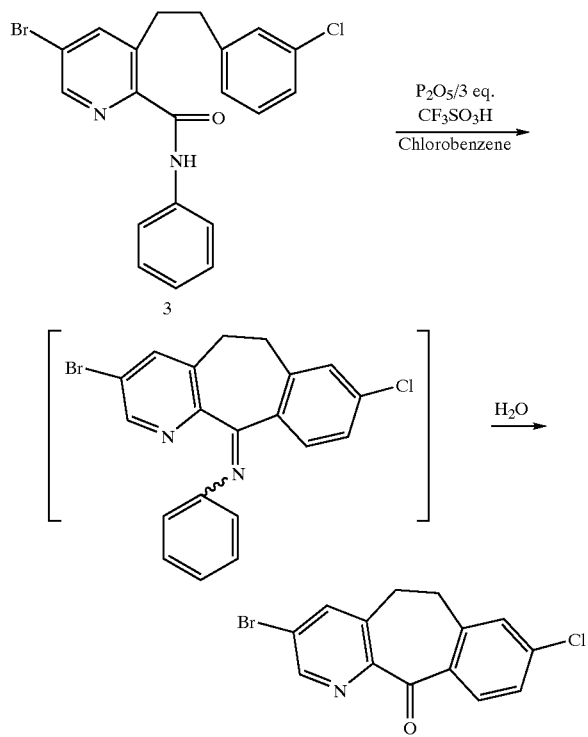

To a 3 L oven-dried three-necked flask equipped with a mechanical stirrer, a thermometer, and an addition funnel were added 100 g (241 mmol) of amide 3, 137 g (963 mmol) of phosphorous pentoxide, and 700 mL of chlorobenzene. To the above slurry was added dropwise 64.2 mL (722 mmol) of trifluoromethanesulfonic acid while maintaining the temperature below 35° C. The resulting mixture was heated to between 80 and 85° C. and stirred at that temperature for about 20 hours. The mixture was cooled to 45° C. and 102 g (722 mmol) of phosphorous pentoxide in 300 mL of chlorobenzene was added. The mixture was heated to 80–85° C. for another 20 hours. To the resulting mixture at 10° C. was added 500 mL of water. The hydrolysis was accomplished by heating the mixture to 70° C. for 2 hours. The reaction mixture was cooled to room temperature and 200 mL of n-butanol (n-BuOH) was added. The layers were separated and the organic layer was washed with brine, diluted sodium hydroxide solution, and diluted HCl solution. The organic layer was concentrated to 300 mL. Addition of 500 mL of THF and 2.4 eq. of concentrated HCl precipitated the product. The solid was filtered, washed with cold n-BuOH, and dried to give 61.7 g (71%) cyclized ketone as HCl salt. Analysis was carried out on the free base. Mp 119–120° C. $^1$H NMR (CDCl$_3$) δ 8.66 (d, J=2.0 Hz, 1H), 7.96 (d, J=8.0 Hz, 1H), 7.75 (d, J=1.5 Hz, 1H), 7.27 (dd, J=8.0, 2.0 Hz, 1H), 7.18 (d J=1.0 Hz, 1H), 3.17–3.09 (m, 4H), 13C NMR (CDCl$_3$) δ 192.7, 153.3, 150.6, 143.8, 140.7, 140.1, 139.3, 136.2, 133.9, 130.6, 128.4, 124.4, 35.4, 33.5. IR (KBr, Nujol) 1660, 1590, 1290 cm$^{-1}$. Anal. Calcd for C$_{14}$H$_9$BrClNO: C, 52.11; H, 2.80; N, 4.34; Br, 24.80; Cl, 11.00. Found: C, 52.03; H, 2.82; N, 4.38; Br, 24.95; Cl, 10.90.

EXAMPLE 2

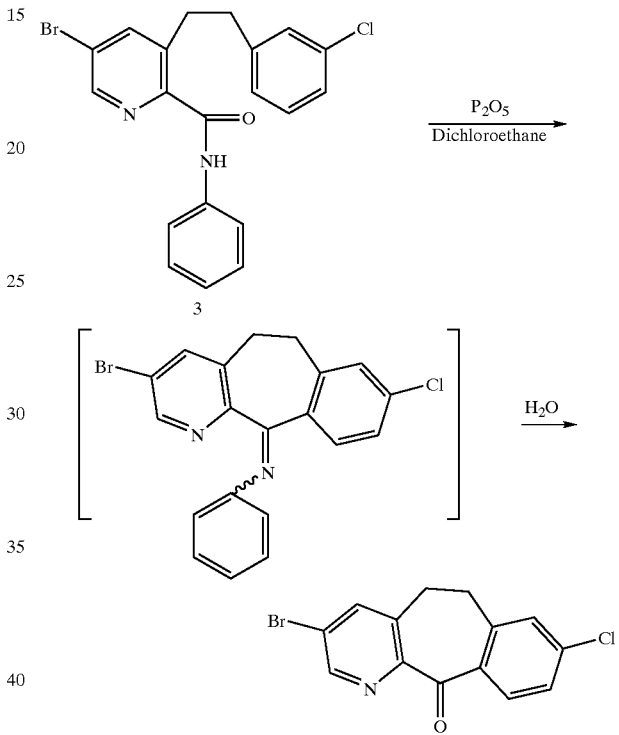

To a three-necked oven-dried 250 mL flask with a mechanical stirrer add 68.35 g (481 mmol) of P$_2$O$_5$, 170 mL of dichloroethane, and 10 g (24 mmol) of amide 3. Heat the mixture to 55 to 60° C. for 16 hours to give about 70% of imine product as determined by HPLC versus a standard. Using the procedure described in Example 1, hydrolyze the imine to obtain the desired tricyclic ketone.

EXAMPLE 3

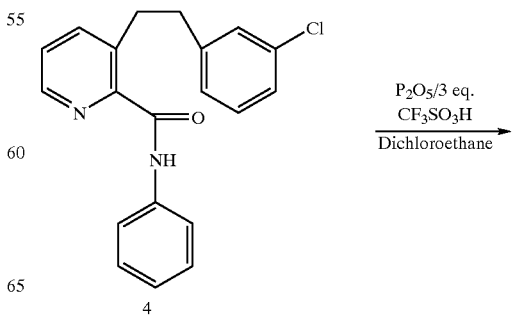

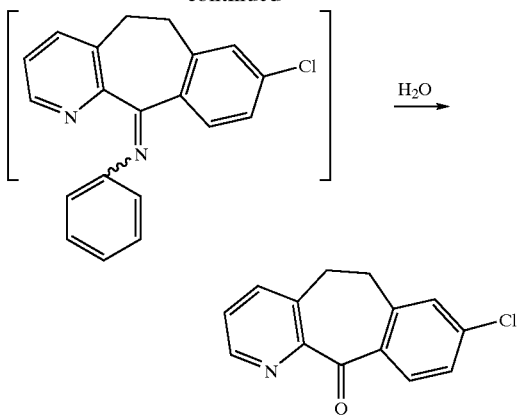

To a 250 mL oven-dried three-necked flask with a mechanical stirrer, a thermometer and an addition funnel were added 250 mL of dichloroethane, 4.2 g of $P_2O_5$ (15 mmol), 2.0 mL (12 mmol) trifluoromethane sulfonic anhydride, and 2.0 mL (30 mmol) of trifluoromethane sulfonic acid. To this mixture was added 5.0 g (14.9 mmol) of the amide 4. The mixture was heated to 80° C. for 18 hours. The mixture was cooled to 10° C. and 70 mL of water was added. The hydrolysis was completed at 70° C. for 1 hour. The reaction mixture was cooled to room temperature and the pH of the reaction mixture was adjusted to 5–6 with sodium hydroxide. The layers were separated and the aqueous layer was extracted with t-butyl methyl ether (t-BuOMe). The combined organic layer was sequentially washed with $NH_4Cl$ and $NaHCO_3$ solutions, and concentrated to a residue. Addition of t-BuOMe precipitated the product. The solid was filtered and washed with cold t-BuOMe and dried to give 2.4 g (68.5%) yellow solid. An NMR spectrum of the product matches that of a reference for the desired tricyclic ketone.

EXAMPLE 4

8-Chloro-5,6-dihydro-11H-benzo[5,6]cyclohepta[1,2-b]pyrid-11-one

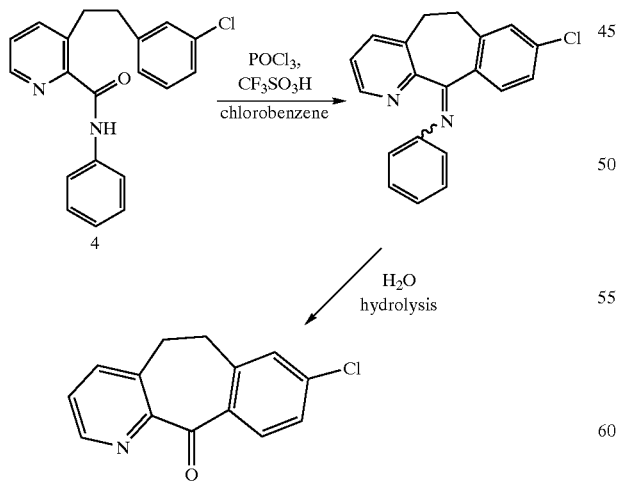

A mixture of triflurorormethanesulfonic acid (63.2 ml; 0.71 mol) and phosphorus oxychloride (66.4 ml; 0.71 mol) in chlorobenzene (400 ml) was stirred for ½hour at room temperature. A solution of N-phenyl-3-[2-(3-chlorophenyl) ethyl]-2-pyridine carboxamide 4 (120 g; 0.36 mol) in chlorobenzene (240 ml) was added. The mixture was heated at 110° C. for 18 hours followed by cooling to 50° C. Water (400 ml) was added and the biphasic mixture heated to 80° C. for ½ hour. The mixture was cooled to room temperature, stirred vigorously for 10 minutes, then allowed to stand for 10 minutes. The product was removed by filtration and partitioned between water (300 ml) and toluene (500 ml). The pH of the aqueous phase was adjusted to 10 with 10M NaOH solution. 100 ml of the organic phase was removed by distillation under reduced pressure. Charcoal (5.5 g) was added and the mixture filtered through a pad of celite. The solution was concentrated under vacuum to 300 ml and 150 ml of hexane was added. The mixture was cooled to 0–10° C. for 1 hour with stirring prior to filtration. The product was washed with 100 ml of chilled toluene and then air-dried for several hours. Yield 44.1 g (50.8%)

EXAMPLE 5

8-Chloro-5,6-dihydro-11H-benzo[5,6]cyclohepta[1,2-b]pyrid-11-one

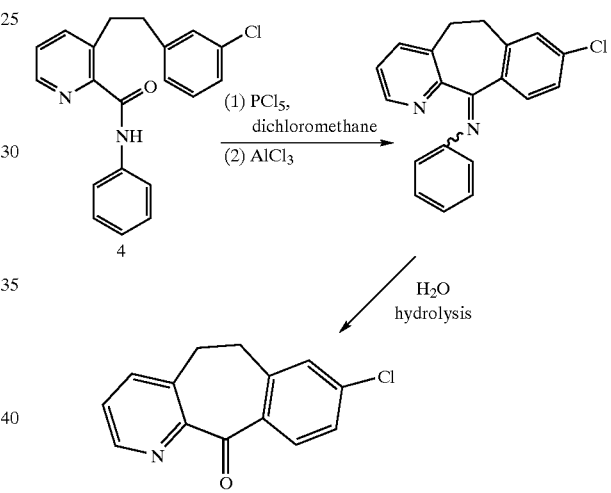

Phosphorous pentachloride (95%, 97.5 g; 0.45 mol) was added to a solution of N-phenyl-3-[2-(3-chlorophenyl) ethyl]-2-pyridine carboxamide 4 (10 g; 0.30 mol) in dichloromethane (500 ml). The resulting mixture was stirred at room temperature for one hour. Aluminum chloride (158.5 g; 1.19 mol) was then added to the mixture followed by stirring at room temperature for one hour. The solution was then poured onto ice (500 g) and the resulting mixture heated to reflux for one hour before cooling to room temperature. The pH of the aqueous phase was adjusted to 14 with 10M sodium hydroxide (700 ml) and the resting suspension filtered through a sintered glass funnel. The collected solid was washed with dichloromethane (2×100 ml). The organic layer of the filtrate was separated and washed with 1M HCl (1×200+1×100 ml). The organic layer was concentrated to an oil under vacuum, toluene (100 ml) was added, and the mixture again concentrated under vacuum. The oil was dissolved in toluene (150 ml) and charcoal (3.5 g) was added. The mixture was filtered through a pad of celite followed by the addition of hexane (100 ml) to the filtrate. The mixture was cooled to 0° C. for one hour prior to filtration. The collected product was dried in a vacuum oven at 60° C. overnight. Yield 44.2 g (61%)

EXAMPLE 6

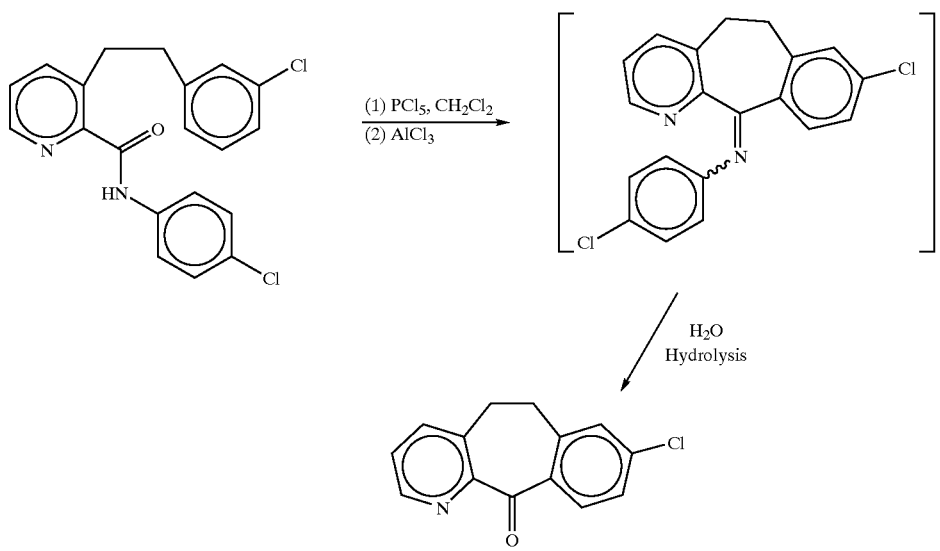

To a solution of phosphorous pentachloride (95%, 26.6 g; 0.121 mol) in dichloromethane (60 ml) at 5° C. was added a solution of N-(4-chlorophenyl)-3-[2-(3-chlorophenyl) ethyl]-2-pyridine carboxamide (30 g; 0.081 mol) in dichloromethane (60 ml) dropwise over 20 minutes. The resulting mixture was stirred at 5 to 10° C. for one hour, then allowed to warm to room temperature over thirty minutes. Aluminum chloride (43.1 g; 0.323 mol) was added in four portions over 45 minutes while maintaining a reaction temperature below 30° C. The mixture was stirred for one hour, then poured onto ice (300 g). The dichloromethane was removed from the mixture by distillation followed by heating the remaining aqueous solution to 80° C. for one hour. Citric acid trisodium salt dihydrate (70 g; 0.24 mol) was added followed by aqueous sodium hydroxide solution (10M, 140 ml) to adjust the pH to 7. Toluene (150 ml) was added, followed by a solution of maleic anhydride (12.0 g 0.122 mol) in toluene (50 ml). The resulting mixture was stirred for 30 minutes and the pH of the aqueous phase adjusted to 12 with aqueous sodium hydroxide solution (10M, 60 ml). The mixture was heated to 70° C. and the phases separated. The aqueous phase was further extracted with toluene (2×90 ml) and the combined organic layers washed with water (90 ml). An HPLC assay indicated a solution yield of ketone product of 95%. The product mixture was recrystallised from toluene/hexane to give the desired tricyclic ketone (13.96 g, 71%) as an off-white solid.

EXAMPLE 7

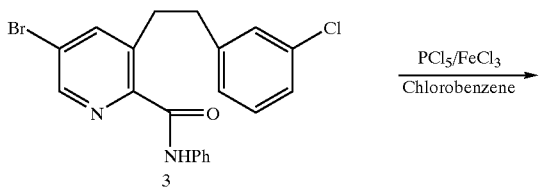

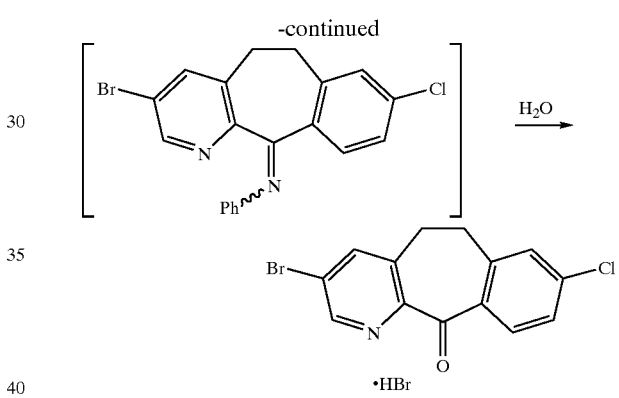

To a 250 mL three-necked flask equipped with magnetic stirrer, thermometer, and reflux condenser were charged 5 g (85.5 mmol) of sodium chloride, 20 g (45.7 mmol) of the amide 3, and 100 mL of chlorobenzene. The mixture was stirred at room temperature under nitrogen for 15 minutes. To the resulting solution was added 16 g (76.8 mmol) of $PCl_5$, while keeping the temperature below 40° C. The reaction mixture was then agitated at 30 to 35° C. for 2 hours. After addition of 15.6 g (96.2 mmol) of $FeCl_3$, the reaction mixture was heated to between 30 and 35° C. for 3 hrs and then to 80 and 85° C. for about 18 hours as followed by HPLC. The reaction mixture was cooled to between 10 and 20° C. and 50 mL of acetone was added. The mixture was agitated for 15 minutes and poured slowly into 200 mL of an aqueous solution of 30 g (224 mmol) of D, L-malic acid. After stirring at room temperature for 1 hour, the product was extracted sequentially with 200 mL and then 100 ml of EtOAc. The combined organic layer was washed with a 200 mL aqueous solution of 20 g (149 mmol) of D, L-malic acid. To the combined organic layer were added 50 mL of acetone, 20 mL of MeOH, and 10 mL of 48% HBr (88 mmol) solution. The mixture was stirred at 45° C. for 2 hours to complete the hydrolysis and then cooled to between 5 and 10° C. with an ice-bath. The precipitate was filtered, washed with 50 mL of acetone, and dried at 25° C. in a vacuum oven to give 16.1 g (82%) of the cyclized product.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the formula

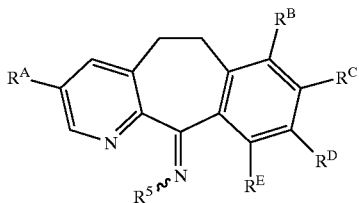

wherein $R^A$, $R^B$, $R^C$, $R^D$, and $R^E$ are independently selected from the group consisting of H, halo, alkyl, or alkoxy, and $R^5$ is aryl or heteroaryl.

2. The compound of claim 1, wherein $R^5$ is phenyl, 4-methoxyphenyl, 4-chlorophenyl, or 3-chlorophenyl, and wherein $R^A$, $R^B$, $R^C$, $R^D$, and $R^E$ are independently selected from the group consisting of H and halo.

3. The compound of claim 2, wherein $R^A$, $R^B$, $R^D$, and $R^E$ are each H, and $R^C$ is Cl.

4. The compound of claim 2, wherein $R^B$, $R^D$, and $R^E$ are H, $R^A$ is Br, and $R^C$ is Cl.

5. The compound of claim 2, wherein $R^A$ and $R^E$ are each Br, $R^B$ and $R^D$ are each H, and $R^C$ is Cl.

* * * * *